US008816151B2

(12) United States Patent
She et al.

(10) Patent No.: US 8,816,151 B2
(45) Date of Patent: Aug. 26, 2014

(54) STAT5B TRANSGENIC MICE AND METHODS OF USE THEREOF

(71) Applicant: Georgia Health Sciences University Research Institute, Inc., Augusta, GA (US)

(72) Inventors: Jin-Xiong She, Martinez, GA (US); Bo Chen, Martinez, GA (US)

(73) Assignee: Georgia Regents Research Institute, Inc., Augusta, GA (US)

( * ) Notice: Subject to any disclaimer, the term of this patent is extended or adjusted under 35 U.S.C. 154(b) by 0 days.

(21) Appl. No.: 13/761,984

(22) Filed: Feb. 7, 2013

(65) Prior Publication Data
US 2013/0212715 A1  Aug. 15, 2013

Related U.S. Application Data

(60) Provisional application No. 61/596,971, filed on Feb. 9, 2012.

(51) Int. Cl.
| | | |
|---|---|---|
| *A01K 67/027* | (2006.01) | |
| *G01N 33/574* | (2006.01) | |
| *A61K 31/277* | (2006.01) | |
| *A61K 31/12* | (2006.01) | |
| *G01N 33/68* | (2006.01) | |
| *A61K 31/353* | (2006.01) | |

(52) U.S. Cl.
CPC .... *G01N 33/6893* (2013.01); *A01K 2267/0362* (2013.01); *G01N 33/57407* (2013.01); *A61K 31/277* (2013.01); *A01K 67/0275* (2013.01); *A61K 31/12* (2013.01); *G01N 33/57426* (2013.01); *G01N 2800/52* (2013.01); *A61K 31/353* (2013.01)
USPC ......... 800/18; 800/9; 800/3; 424/9.1; 424/9.2

(58) Field of Classification Search
None
See application file for complete search history.

(56) References Cited

U.S. PATENT DOCUMENTS

| | | | |
|---|---|---|---|
| 2008/0118518 A1* | 5/2008 | Cirrito et al. | 424/155.1 |
| 2009/0061022 A1 | 3/2009 | Lee | |
| 2010/0209929 A1 | 8/2010 | Fantl | |

FOREIGN PATENT DOCUMENTS

WO 2007047955 4/2007

OTHER PUBLICATIONS

Shmerling et al. "Strong and Ubiquitous Expression of Transgenes Targeted Into the b-Actin Locus by Cre/lox Cassette Replacement." genesis(2005); 42: pp. 229-235.*
Barrick et al. "Cardiac response to pressure overload in 129S1/SvImJ and C57BL/6J mice: temporal- and background-dependent development of concentric left ventricular hypertrophy." Am J Physiol Heart Circ Physiol (2007); 292: pp. H2119-H2130.*
Miyagawa et al. "Remodeling of the Major Pig Xenoantigen by N-Acetylglucosaminyltransferase III in Transgenic Pig." The Journal of Biological Chemistry (2001); 276 (42): pp. 39310-39319.*
Shuringa et al. "Constitutive Activation of STAT5A Promotes Human Hematopoietic Stem Cell Self-Renewal and Erythroid Differentiation." The Journal of Experimental Medicine (2004); 200 (5): pp. 623-635.*
Vogtenhuber et al. "Constitutively active Stat5b in CD4 T cells inhibits graft-versus-host disease lethality associated with increased regulatory T-cell potency and decreased T effector cell responses." Blood (2010); 116 (3): pp. 466-474.*
Nelson et al. "The STAT5 inhibitor pimozide decreases survival of chronic myelogenous leukemia cells resistant to kinase inhibitors." Blood (2011); 117(12): pp. 3421-3429.*
Nelson et al. "The STAT5 inhibitor pimozide decreases survival of chronic myelogenous leukemia cells resistant to kinase inhibitors." Supplemental pp. 1-9.*
Lewis et al. "Establishment of a Reproducible Model of Chronic-Phase Chronic Myeloid Leukemia in NOD/SCID Mice Using Blood-Derived Mononuclear or CD341 Cells." Blood(1998); 91(2 ): pp. 630-640.*
Aifantis, et al., "Molecular pathogenesis of T-cell leukaemia and lymphoma" , Nature Rev., 8(5):380-90 (2008).
Bessette, et al., "A Stat5b transgene is capable of inducing CD8+ lymphoblastic lymphoma in the absence of normal TCR/MHC signaling" , Blood, 111(1):344-50 (2008).
Carron, et al., "TEL-JAK2 transgenic mice develop T-cell leukemia" , Blood, 15:95(12):3891-9 (2000).
Cheon and Stark, "Unphosphorylated STAT1 prolongs the expression of interferon-induced immune regulatory genes" , PNAS, 106(23):9373-8 (2009).
dos Santos, et al., "Pre-TCR expression cooperates with TEL-JAK2 to transform immature thymocytes and induce T-cell leukemia" , Blood, 109 (9):3972-81 (2007).
Gerhauser, et al., "Cancer chemopreventive activity of Xanthohumol, a natural product derived from hop" , Mole Cancer Therap., 1(11):959-69 (2002).
Heinzerling, et al., "Oncolytic measles virus in cutaneous T-cell lymphomas mounts antitumor immune responses in vivo and targets interferon-resistant tumor cells" , Blood, 106(7):2287-94 (2005).
Kabbarah and Chin, "Revealing the genomic heterogeneity of melanoma" , Cancer Cell, 8(6):439-41 (2005).
Kelly, et al., "A role for Stat5 in CD8+ T cell homeostasis" , J Immunol., 1:170 (1):210-7 (2003a).
Kelly, et al., "Stat5 synergizes with T cell receptor/antigen stimulation in the development of lymphoblastic lymphoma" , J Exp Med., 198(1):79-89 (2003).
Kerr, "Comments on the analysis of unbalanced microarray data" , Bioinformatics, 15;25(16):2035-41 (2009).
Klinger, et al., Deregulated expression of RasGRP1 initiates thymic lymphomagenesis independently of T-cell receptors. Oncogene. 24 (16):2695-2704 (2005).

(Continued)

*Primary Examiner* — Deborah Crouch
*Assistant Examiner* — Titilayo Moloye
(74) *Attorney, Agent, or Firm* — Pabst Patent Group LLP

(57) ABSTRACT

It has been discovered that STAT5 phosphorylation and CD150 are effective biomarkers for detecting, diagnosing, and monitoring hematological malignancies, including for example lymphomas. Compositions and methods for identifying therapeutic agents for the treatment of hematologic malignancies using p-STAT5, CD150 or both as biomarkers are described.

3 Claims, 7 Drawing Sheets

(56) References Cited

OTHER PUBLICATIONS

Lebigot, et al., "Up-regulation of SLAP in FLI-1-transformed erythroblasts interferes with EpoR signaling", Blood, 102(13):4555-62 (2003).

Moriggl, et al., "Stat5 tetramer formation is associated with leukemogenesis", Cancer Cell, 7(1),:87-99 (2005).

Muller, et al., "Discovery of chromone-based inhibitors of the transcription factor STAT5", Chembiochem., 9(5):723-7 (2008).

Nikitakis, et al., "Targeting the STAT pathway in head and neck cancer: recent advances and future prospects", Curr Cancer Drug Targets, 4(8):637-51 (2004).

Pecquet, at al., "Constantinescu SN. Induction of myeloproliferative disorder and myelofibrosis by thrombopoietin receptor W515 mutants is mediated by cytosolic tyrosine 112 of the receptor", Blood, 115(5):1037-1048, Feb. 2010.

Rouet, et al., "Local prolactin is a target to prevent expansion of basal/stem cells in prostate tumors", PNAS, 107(34):15199-204 (2010).

Schwaller, et al., "Stat5 is essential for the myelo- and lymphoproliferative disease induced by TEL/JAK2", Molecular Cell, 6(3):693-704 (2002).

Serwold, et al., "T-cell receptor-driven lymphomagenesis in mice derived from a reprogrammed T cell", PNAS, 107(44):18939-43 (2010).

Shukla and Gupta, "Apigenin: a promising molecule for cancer prevention", Pharma. Res., 27(6):962-78 (2010).

Smyth, "Linear models and empirical bayes methods for assessing differential expression in microarray experiments", Stat. Appl. Genet Mol Biol., 3:Article3 (2004).

Sordella, et al., "Gefitinib-sensitizing EGFR mutations in lung cancer activate anti-apoptotic pathways", Science, 305(5687)1163-7 (2004).

Tang, et al., "Signal transducer and activator of transcription (STAT)-5A and STAT5B differentially regulate human mammary carcinoma cell behavior", Endocrin.,151(1):43-55, Jan. 2010.

Wang, et al., "The costimulatory molecule SLAM is critical for pulmonary allergic responses", Am J Respir Cell Mol Biol., 35(2):206-10 (2006).

Wang, et al., "Adaptive secretion of granulocyte-macrophage colony-stimulating factor (GM-CSF) mediates irnatinib and nilotinib resistance in BCR/ABL+ progenitors via JAK-2/STAT-5 pathway activation", Blood, 109(5):2147-55 (2007).

Yao, et al., "Stat5a/b are essential for normal lymphoid development and differentiation", PNAS, 103(4)1000-5(2006).

Yu, et al., "Constitutive activation of the Janus kinase-STAT pathway in T lymphoma overexpressing the Lck protein tyrosine kinase", J Immunol., 159(11):5206-10 (1997).

Zawistowski, et al., "Extending rare-variant testing strategies: analysis of noncoding sequence and imputed genotypes", Am J Human Genetics, 87 (5):604-17, Nov. 2010.

Dell\Eva, er al., "AKT/NF-kappaB inhibitor xanthohumol targets cell growth and angiogenesis in hematologic malignancies", Cancer, 110(9):2007-11 (2007).

Laloraya, et al., Impaired Crkl expression contributes to the defective DNA binding of Stat5b in nonobese diabetic mice, Diabetes, 55(3):734-41 (2006).

Spiekermann, et al., "Constitutive activation of STAT transcription factors in acute myelogenous leukemia", Eur. J Haematol., 67(2):6371 (2001).

Tang, et al., "Synthesis and structural determination of multidentate 2,3-dithiol-stabilized au cluster", J Am Chem Soc., 132:3357-74 (2010).

Zhao, et al., Apigenin inhibits proliferation and induces apoptosis in human multiple myeloma cells through targeting the trinity of CK2, Cdc37 and Hsp90, Mole Cancer, 10:104. doi: 10.1186/1476-4598-10-104 (2011).

International Search Report and Written Opinion for PCT/US2013/025143 mailed Jun. 6, 2013.

* cited by examiner

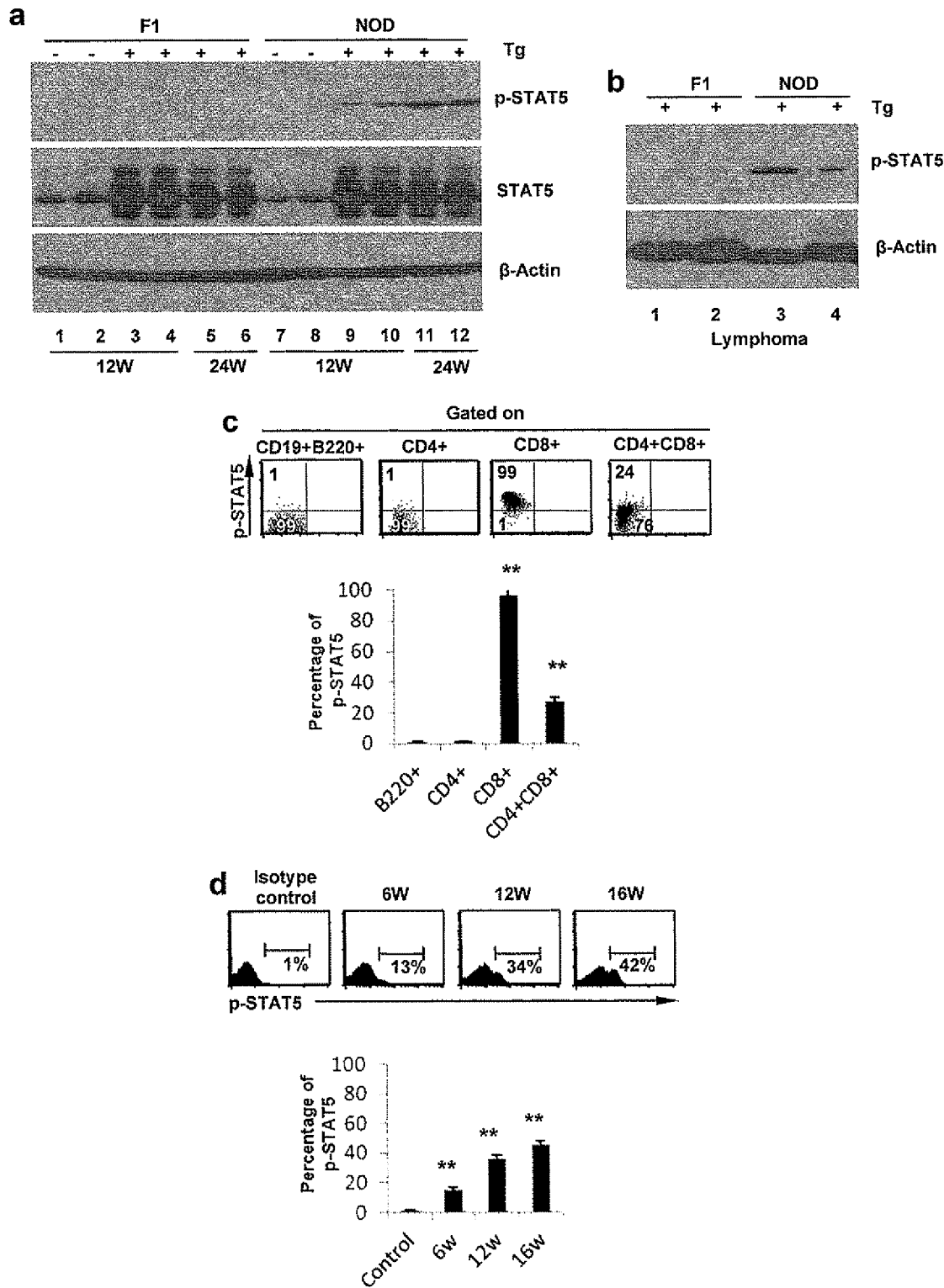
FIG. 3A, FIG. 3B, FIG. 3C, and FIG. 3D

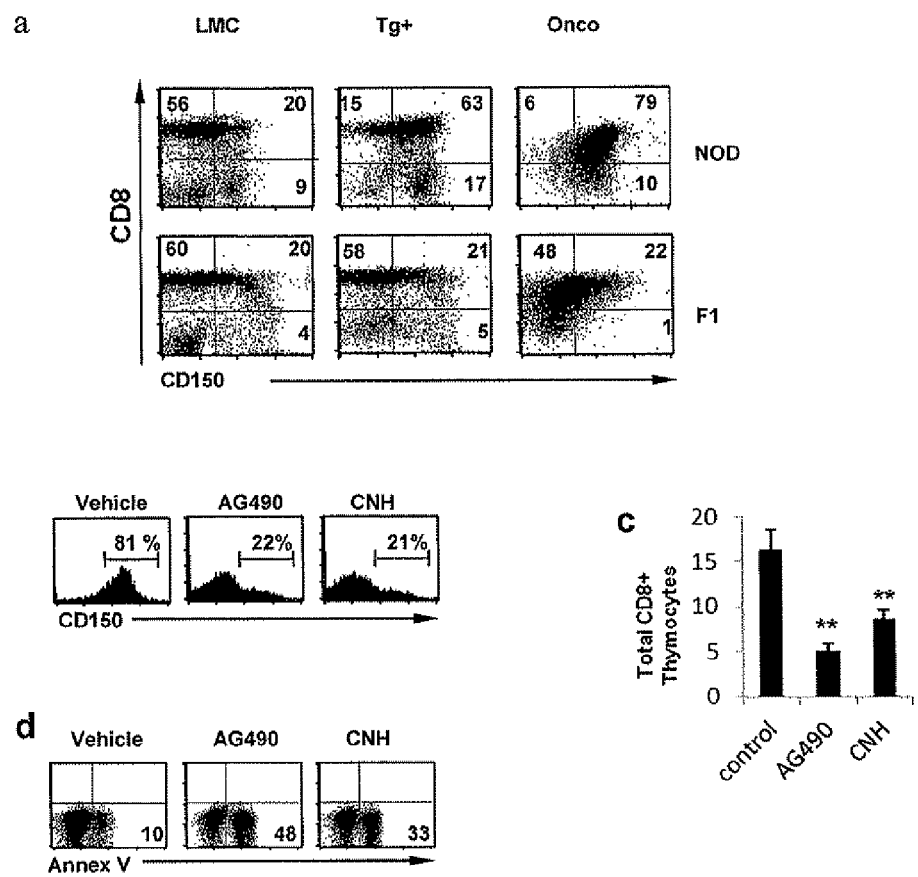
FIG. 5A, FIG. 5B, FIG. 5C, and FIG. 5D

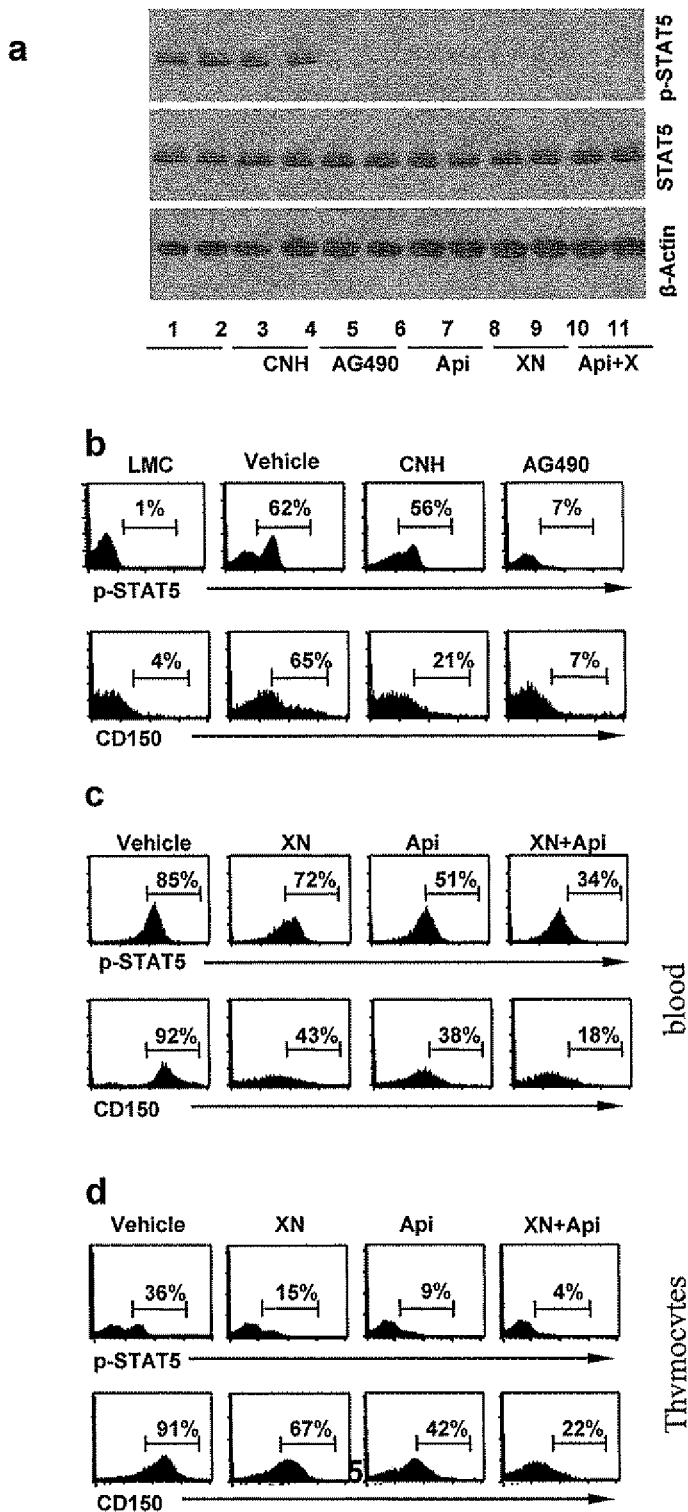
FIG. 6A, FIG. 6B, FIG. 6C, and FIG. 6D

STAT5B TRANSGENIC MICE AND METHODS OF USE THEREOF

FIELD OF THE INVENTION

The invention is generally directed to methods and compositions for the detection, diagnosis or treatment of hematologic malignancies, in particular, the use of CD150 as a biomarker in the diagnosis or treatment of lymphoma.

BACKGROUND OF THE INVENTION

Lymphoma, including Hodgkin lymphoma and non-Hodgkin lymphoma (NHL), represents approximately 5 percent of all cancers in the United States. It is estimated that approximately $10.2 billion is spent in the United States each year on lymphoma treatment (Cancer Trends Progress Report, progressreport.cancer.gov). The National Cancer Institute estimates 70,130 new cases and 18,940 deaths from non-Hodgkin lymphoma in the United States in 2012: It is estimated that approximately 9,060 new cases will be diagnosed and 1,190 deaths will result from Hodgkin lymphoma in the United States in 2012:

Therefore, it is an object of the invention to provide methods and compositions for detecting or diagnosing lymphoma.

It is another object of the invention to provide methods and compositions for identifying therapeutic agents for treating lymphoma.

SUMMARY OF THE INVENTION

It has been discovered that STAT5 phosphorylation and CD150 are effective biomarkers for detecting, diagnosing, and monitoring hematological malignancies, including for example lymphomas. Compositions and methods for identifying therapeutic agents for the treatment of hematologic malignancies using STAT5-p, CD150 or both as biomarkers are described.

The data described in the Examples demonstrates that lymphomagenesis can be reduced, inhibited, or prevented by inhibiting STAT5b activation, downregulating expression of CD150, or both in immune cells in an animal model that spontaneously develops lymphomas. Non-obese diabetic (NOD) mice with the Stat5b transgene and that have a high incidence of CD8$^+$ T cell lymphoma with earlier age of onset were developed. The selective activation of STAT5b and expression of CD150 in CD8$^+$ T cells in the NOD genetic background was discovered to be responsible for lymphomagenesis. Blocking STAT5b phosphorylation and CD150 expression using specific inhibitors for the STAT5 pathway or cancer chemoprevention agents that inhibit STAT5 activation and CD150 expression efficiently prevents lymphomagenesis in this model.

Methods for identifying therapeutic agents for the treatment of hematological malignancies are provided. The method includes administering a test compound to the disclosed transgenic animals and determining the presence or absence of hematological malignancies or symptoms thereof in the transgenic animal after administration of the test compound. A reduced amount of hematological malignancies or symptoms thereof in the transgenic animal after treatment with the test compound is indicative that the test compound is a therapeutic agent for the treatment of the hematological malignancies.

Methods for detecting or diagnosing hematologic malignancies or the risk of developing hematologic malignancies are also provided. The methods include determining the presence of p-STAT5, CD150, or both in immune cells in a sample from a subject, wherein an increased presence of p-STAT, CD150 or both in the immune cells in the sample from the subject is indicative of a hematological malignancy or is indicative of an increased risk of the subject developing a hematological malignancy relative to a control. Exemplary hematological malignancies include, but are not limited to leukemia, lymphoma, and myeloma.

Leukemias include acute lymphoblastic leukemia (ALL), acute myelogenous leukemia (AML), chronic lymphocytic leukemia (CLL), small lymphocytic lymphoma (SLL), chronic myelogenous leukemia (CML), and acute monocytic leukemia (AMOL).

Lymphomas include Hodgkin's lymphomas and Non-Hodgkin's lymphomas. NHL can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma.

Methods for treating a subject having or suspected of having a hematological malignancy are also provided. The methods include administering to the subject an effective amount of an inhibitor of the STAT5 pathway to inhibit or reduce expression of CD150 on immune cells. Suitable inhibitors of the STAT5 pathway include AG490, CNH, or a combination thereof. The inhibitor of STAT5 phosphorylation can be administered in combination with an anti-cancer agent. Representative anti-cancer agents include xanthohumal, apigenin, and combinations thereof.

Another method for treating a subject having or suspected of having a hematological malignancy includes administering to the subject an effective amount of an anticancer agent to reduce expression of CD150 on CD8+ cells to treat one or more symptoms of the hematological malignancy.

Other methods that are described include methods for determining the efficacy of a treatment for a hematological malignancy on a subject having a hematological malignancy. Typically, the method includes determining the presence of p-STAT5, CD150, or both, in or on immune cells in a sample from the subject undergoing the treatment, wherein an increased presence of p-STAT, CD150 or both in or on the immune cells in the sample from the subject relative to a control is indicative that the treatment for the hematological malignancy is ineffective for the subject.

Another embodiment provides a transgenic mammal overexpressing a constitutively active form of STAT5. The activated form of STAT5 is the phosphorylated form of STAT5. The preferred active form of STAT5 is STAT5b (i.e. phosphorylated STAT5b). The transgenic mammal is typically a mouse, and is preferably a NOD mouse.

BRIEF DESCRIPTION OF THE DRAWINGS

FIG. 1a is a line graph of lymphoma frequency versus age (weeks) observed in F1.Stat5b$^{Tg}$ mice (▲) (n=15), NOD.Stat5b$^{Tg}$ mice (●) (n=46) without treatment, and NOD.Stat5b$^{Tg}$ mice after treatment with Epi/XN (■) (n=16) or CNH (♦) (n=12). FIG. 1b are photographs of a mouse that has enlarged thymus, spleen, and lymph nodes (left panel). Enlarged spleen (SP), cervical lymph node (CN) and thymus (Thy) are compared to littermate controls (right panel). The inset charts compare the weight (Mg) of spleen (SP), thymus (Thy) and cervical nodes (CN) between mice with tumors and littermate controls (LMC). **P<0.01. FIG. 1c are micrographs of H&E staining of spleen, cervical node and thymus from a NOD.Stat5b$^{Tg}$ mouse with lymphoma. Scale bars represent 50 um.

FIG. 2a has three different flow cytometry dot plots of CD4+ versus CD8+ cells showing the types of lymphoma cells observed in NOD.Stat5b$^{Tg}$ mice. The vast majority of lymphomas (57/60) are similar to the Onco 2 mouse, e.g., with CD4$^+$CD8$^+$ double positive and CD8$^+$ single positive thymocytes. Two mice with lymphomas had predominantly CD8$^+$ single-positive thymocytes (Onco 18) and one mouse had predominantly CD4$^+$CD8$^+$ double-positive thymocytes (Onco 29). FIG. 2b is a bar graph of total number of thymocytes (millions) observed in wildtype NOD mice (open square), transgenic NOD mice (solid square), wildtype F1 mice (hatched), and transgenic F1 mice (cross-hatched) of mice at 6 and 12 weeks of age. FIG. 2c are flow cytometry dot plots CD4+ versus CD8+ cells showing T cell phenotypes in the thymus (Thy) of NOD.Stat5b$^{Tg}$ and F1.Sta5b$^{Tg}$ mice compared to their wild type (WT) control at 6 weeks (6 w) and 12 weeks (12 w) of age. Representative data are shown from 1 of 4 similar experiments.

FIG. 3a shows representative Western blotting analysis for phosphorylated and total STAT5 in F1 and NOD Stat5b transgenic lines. These mice did not have detectable signs of lymphoma based on physical examination and FACS analysis of T cell phenotypes. Protein extracts from thymus were used for the experiment. FIG. 3b shows representative Western blotting analysis of phosphorylated STAT5 with thymus protein extracts from F1 and NOD Stat5b transgenic mice with lymphoma. FIG. 3c shows STAT5 phosphorylation status in different cell types. Thymocytes and splenocytes from NOD.Stat5b$^{Tg}$ mice were analyzed by intracellular staining for phosphorylated STAT5 with an anti-pTyr694-STAT5 antibody. , P<0.01 compared with B220$^+$ and CD4$^+$ Cells. FIG. 3d is FACS analysis showing progressive increase of STAT5 phosphorylation in thymocytes of NOD.Stat5b$^{Tg}$ mice. Data for thymus are shown here for 6, 12 and 16 week old NOD.Stat5b$^{Tg}$ mice (all without tumor), P<0.01, compared with isotype control. Representative data are shown from 1 of 3 similar experiments.

FIGS. 5a-d show the expression of CD150 in NOD and F1.Stat5b$^{Tg}$ mice and the effect of the STAT5 inhibitors. FIG. 5a is a panel of flow cytometry dot plots showing CD150 expression on the surface of CD8$^+$ thymocytes of NOD.Stat5b$^{Tg}$ and F1.Stat5b$^{Tg}$ mice with (Onco), transgenic (Tg+) and non-transgenic littermate control (LMC) without lymphoma. The LMC and TG+ mice were at 6 weeks of age. FIG. 5b are histograms showing CD150 expression on surface of thymocytes from NOD.Stat5b$^{Tg}$ mice after treatment with vehicle, AG490 or CNH. FIG. 5c is a bar graph showing total numbers (10$^6$) of CD8$^+$ thymocytes after treatment with vehicle (Control), AG490 or CNH for 2 weeks. **P<0.01 for comparison with control. FIG. 5d are dot plots showing Annex V levels (apoptosis) in lymphoma cells after treatment with AG490 or CNH in hallow fiber assay.

FIGS. 6a-d show expression of p-STAT5 and CD150 in NOD Stat5b$^{Tg}$ mice. FIG. 6a shows representative Western blotting analysis of phosphorylated STAT5 with thymus protein extracts from NOD.Stat5b$^{Tg}$ after treatment. FIG. 6b is a panel of histograms showing pSTAT5 and CD150 expression in CD8$^+$ peripheral blood T cells from non-transgenic littermate control (LMC) and NOD.Stat5b$^{Tg}$ mice treated with vehicle, CNH or AG490 for 2 weeks. Data were obtained by FACS analysis. FIG. 6c is a panel of histograms showing pSTAT5 and CD150 expression in CD8$^+$ peripheral blood T cells from NOD.Stat5b$^{Tg}$ mice treated with vehicle, XN, Api or XN+Api for 2 weeks. FIG. 6d is a panel of histograms showing pSTAT5 and CD150 expression in CD8$^+$ thymocytes of NOD.STAT5b mice measured by FACS analysis after compound treatment for 2 weeks. Representative data are shown from 1 of 3 similar experiments.

DETAILED DESCRIPTION OF THE INVENTION

Figure 1A:
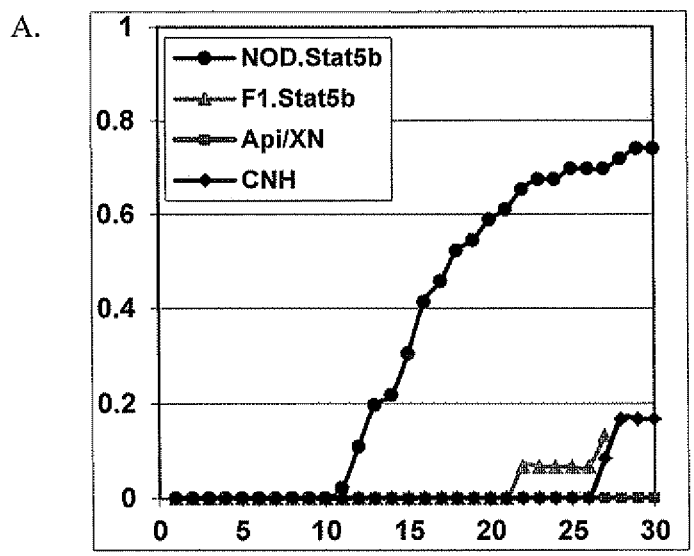
FIGS. 1a-c show lymphoblastic lymphoma in Stat5b transgenic mice.

I. Biomarkers for Hematological Malignancies p-STAT5, CD150, or a combination thereof can be used as biomarkers for the detection or diagnosis of hematological malignancies or for assessing the risk of a subject for developing a hematological malignancy relative to a control. The biomarkers can also be used to monitor the progression of hematological malignancies, monitor the treatment of hematological malignancies, or to screen for agents effective for treating hematological malignancies. The biomarkers are typically found in tumor cells of a subject with a hematological malignancy or in a subject that has an increased risk of developing a hematological malignancy relative to a control. Representative cells that express the biomarkers include, but are not limited to lymphocytes, preferably CD8+ T cells.

A. p-STAT5

The mammalian STAT family contains seven members that play diverse roles in embryonic cell development, differentiation, proliferation, migration, survival and apoptosis. Their activities are regulated by different cytokines, hormones and growth factors. In lymphoid cells, STAT1, 3, 5a and 5b are believed to be responsible for cell survival and growth, while STAT2, 4 and 6 are preferentially involved in differentiation (1). STATs exist as monomers in the cytoplasm before receptor activation (2). Cytokine stimulation leads to Janus kinase (JAK) activation followed by phosphorylation of tyrosine residues in the cytoplasmic domain of the cytokine receptor. Activated JAKs, which phosphorylate the C-terminal tyrosine residue of STATs, lead to STAT dimer formation by the intermolecular interactions of the SH2 domain and the phosphorylated tyrosine (3). Once dimerized, STATs dissociate from the receptors and translocate to the nucleus where they bind to target DNA and regulate gene expression.

STAT5b, a member of the STAT family, has been implicated as an oncogene, consistent with its role in cell proliferation and survival (4-7). It can be activated by multiple cytokines including IL-2, IL-3, IL-5, IL-7, IL-9 and IL-15, various growth factors as well as prolactin, growth hormone and erythropoietin (8). STAT5 can be activated through phosphorylation by tyrosine kinases. The roles of STAT5 in tumorigenesis and drug resistance have been increasingly recognized in the last few years.

Over-expression of STAT5 and phosphorylated STAT5 (p-STAT) have been reported for a variety of cancers including breast, prostate, lung, head and neck, liver, melanoma and lymphomas (9-13). Constitutive activation of STAT5 also predicts drug resistance in T cell lymphoma (14). However, STAT5 activity is associated with better prognosis for survival in breast cancer (15, 16).

The roles of STAT5 in tumorigenesis have also been demonstrated in animal studies. C57BL/6 (B6) mice with a wild-type Stat5b transgene, which is conditionally over-expressed in T, B and NK cells, develops low incidence of CD8+ lymphoblastic lymphoma with characteristics of T cell acute lymphoblastic leukemia/lymphoma (T-ALL) and the rate of lymphomagenesis was markedly enhanced by immunization or the introduction of TCR transgenes (7). However, STAT5b phosphorylation was surprisingly not observed in these transgenic mice with or without lymphomas.

B. CD150

Human signaling lymphocyte activation molecule (SLAM; also called CD150), is a membrane glycoprotein of the immunoglobulin superfamily. SLAM is expressed on immature thymocytes, activated lymphocytes, macrophages and dendritic cells and regulates production of interleukin (IL)-4 and IL-13 by CD4+ T cells, as well as production of IL-12, tumor necrosis factor alpha and nitric oxide by macrophages.

C. p-STAT5 and CD150

It has been discovered that both CD150 and pSTAT5 were highly expressed in peripheral CD8+ T cells of NOD.Stat5b$^{Tg}$ mice (FIGS. 6b & 6c). Furthermore, STAT5 pathway inhibitors decreased the expression of CD150 and pSTAT5 in peripheral CD8+ T cells (FIG. 6b). Thus, one embodiment provides using both markers to detect, diagnosis, or assess the risk of a subject for developing a hematological malignancy. Still another embodiment provides using the NOD.Stat5b$^{Tg}$ mice to screen for agents effective for treating lymphoma.

II. Using p-STAT and CD150 to Screen for Therapeutics

Because STAT5 pathway inhibitors were discovered to decrease the expression of CD150 and p-STAT5 in peripheral CD8+ T cells (FIG. 6b) in NOD.Stat5b$^{Tg}$ mice, these mice are well suited for assisting in the identification of therapeutic agents for the treatment of hematological malignancies, in particular for the treatment of CD8+ T cell lymphoma. For example, a test compound can be administered to a NOD.Stat5b$^{Tg}$ mouse prior to the development of a hematological malignancy or after the mouse has developed a hematological malignancy. The mouse treated with the test compound is monitored for progression or development of the malignancy, and treated mice that show reduced or delayed development of the malignancy indicate that the test compound administered to them is effective for treating the malignancy. The test compound is often used as a lead compound that is chemically modified, for example halogenated or esterified, to produce a therapeutic used to treat hematological malignancies such as lymphoma.

In a preferred embodiment, the transgenic animals are used to assay the effectiveness of a test compound for inhibiting or reducing expression of p-STAT5, CD150, or both in CD8+ immune cells of the transgenic animals. Test compounds that inhibit or reduce the expression of p-STAT5, CD150, or both in CD8+ immune cells of the transgenic animals indicate that the test compound is effective for treating a hematological malignancy such as lymphoma.

Other animal models for studying the development are preferably non-human transgenic animals that express the Stat5b gene.

A. In vivo Screening

In vivo assays to identify therapeutic agents involve the use of the disclosed animal models, including non-human transgenic animals as described herein that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including C. elegans, rats, rabbits, hamsters, guinea pigs, gerbils, woodchucks, cats, dogs, sheep, goats, pigs, cows, horses and monkeys (including chimps, gibbons and baboons). Assays for therapeutic agents may be conducted using an animal model derived from any of these species.

Treatment of these animals with test compounds will involve the administration of the compound, in an appropriate form, to the animal. Administration will be by any route that could be utilized for clinical or non-clinical purposes, including, but not limited to, oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

B. In vitro Screening

Cells from the transgenic animals expressing the Stat5b gene, preferably cells from NOD transgenic mice, can be cultured in vitro and contacted with a test compound to determine the effectiveness of the test compound for inhibiting or reducing p-STAT5, CD150, or both in the cells. Preferred cells for use in the in vitro screen include, but are not limited to peripheral immune cells obtained from the transgenic animal or derived from the transgenic animal. In one embodiment, the cells are CD8+ T cells, more preferably CD8+ T cell lymphoma cells.

Methods for culturing and maintaining cells in culture are known in the art. Methods for assaying the expression of p-STAT5 and CD150 are also known in the art and described in the Examples.

III. Methods for Treating Hematological Malignancies

A. Inhibiting pSTAT, CD150 or Both

Methods for treating one or more symptoms of a hematological malignancy are also provided. Exemplary hematological malignancies include, but are not limited to leukemia, lymphoma, and myeloma.

Leukemias include acute lymphoblastic leukemia (ALL), acute myelogenous leukemia (AML), chronic lymphocytic leukemia (CLL), small lymphocytic lymphoma (SLL), chronic myelogenous leukemia (CML), and acute monocytic leukemia (AMOL).

Lymphomas include Hodgkin's lymphomas and Non-Hodgkin's lymphomas. NHL can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma.

Representative methods of treatment include administering to the subject an effective amount of an inhibitor of the STAT5 pathway to inhibit or reduce expression of CD150 on immune cells. Suitable inhibitors of the STAT5 pathway include AG-490, CNH, or a combination thereof. The inhibitor of STAT5 phosphorylation can be administered in combination with an anti-cancer agent. Representative anti-cancer agents include xanthohumal, apigenin, and combinations thereof.

Another method for treating a subject having or suspected of having a hematological malignancy includes administering to the subject an effective amount of an anticancer agent to reduce expression of CD150 on CD8+ cells to treat one or more symptoms of the hematological malignancy.

Still another method of treating a subject having or suspected of having a hematological malignancy includes administering to the subject an effective amount of an anti-cancer agent to reduce expression of CD150 on CD8+ cells in combination with effective amount of an inhibitor of the STAT5 pathway to treat one or more symptoms of the hematological malignancy.

B. Combination Therapy

In certain embodiments, the methods for treating the hematological malignancy include administering additional therapeutic agents that may or may not inhibit or reduce pSTAT5, CD150 or both. For example, the disclosed therapeutic agents can be administered in combination with known anti-cancer agents.

Representative anti-cancer agents include, but are not limited to chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

EXAMPLES

Example 1

NOD.Stat5b$^{Tg}$ Mice Develop High Incidence of CD8 Lymphoblastic Lymphoma

Material and Methods
Generation of Mice

The Stat5b transgenic mouse in the B6 genetic background (B6.Stat5b$^{Tg}$) was generated as previously described by Kelly et al (7). The Stat5b transgene was under the control of the H-2K$^b$ promoter and heavy-chain enhancer as previously described (25). The transgene was moved from the B6 to the NOD genetic background through 21 generations of backcrossing. The resulting strain (NOD.Stat5b$^{Tg}$) was used for experiments described in this study. NOD/B6 F1 mice used in this study were obtained by breeding the NOD.Stat5b$^{Tg}$ mice with regular B6 mice from the Jackson Laboratory.

Figure 1B:
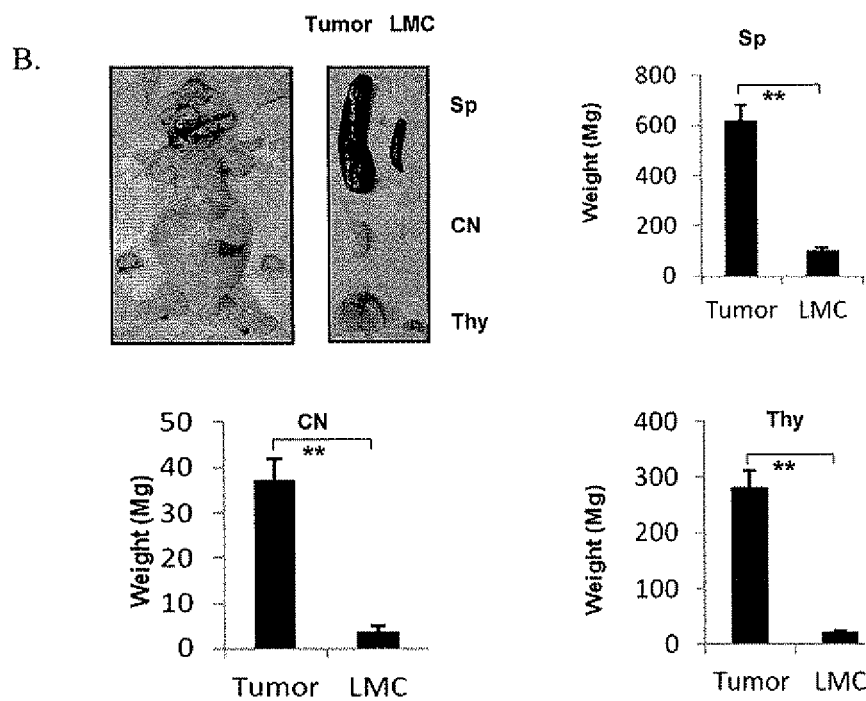
Figure 1C:
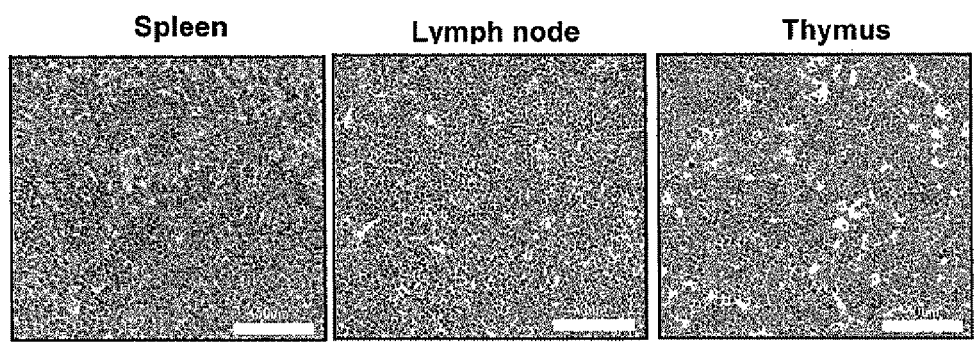

In several experiments, mice were monitored for tumors through physical examination. Mice showing sufficient signs of pain and suffering including thymic and cervical lymphoid enlargement were euthanized for a complete necropsy. Final diagnosis of disease was established by clinical, pathologic and FACS analysis. Images of H&E staining were visualized with an Axiophot I microscope (Carl Zeiss) equipped with a Plan Neofluar 40X objective (FIG. 1c). Images were captured with an Axiocam color CDD camera, and treated on a computer with Axiovision software (Carl Zeiss).

All animal experiments were performed under an Animal Component of Research Protocol (ACORP) approved by the Institutional Animals Care and Use Committees (IACUCs) of the Georgia Health Science University.

Animal Treatment

AG490 (30 mg/kg/day) and STAT5 inhibitor CNH (40 mg/kg/day) purchased from Calbiochem (La Jolla, Calif.) were injected intraperitoneally into F1 and NOD.Stat5b transgenic lines. Xanthohumol and apigenin (>98% purity by HPLC) purchased from Sigma (St. Louis, Mo.) were used in the chemoprevention experiments. Xanthohumol (100 mg/kg/day) and Apigenin (200 mg/kg/day) were injected alone or in combination intraperitoneally into NOD.Stat5b$^{Tg}$ mice.

In vivo Hollow Fiber Assay

Cellmax implant membranes were purchased from Spectrum Laboratories Inc. (Rancho Dominguez, Calif.). Lymphoma cells from NOD.Stat5b$^{Tg}$ mice were harvested, suspended in cold phosphate buffered saline (PBS) and introduced into a 15 cm length of hollow fiber. The fiber was heat-sealed at 20 mm intervals, and each segment was separated using a pair of scissors. Intraperitoneal implantation in methoxyflurane anesthetized 6 week-old nude mice were accomplished via a dorsal incision which allowed passage of the hollow fiber into abdomen. The abdominal wall is closed using skin staples. After 3 days of transplantation, mice with implants were treated daily with either AG490 (30 mg/kg/day) or CNH (40 mg/kg/day). Single cell suspensions were obtained after 4 days of treatment by cutting off the sealed ends of the fibers. Cells were then washed twice with PBS and further processed for flow cytometry.

Flow Cytometry

Single-cell suspensions from thymus, spleen, lymph nodes and hollow fibers were stained and analyzed using a fluorescence-activated cell sorting (FACS) flow cytometer (BD Biosciences) with CELLQuest 3.3 software (Becton Dickinson, San Jose, Calif.). All antibodies were purchased from BD PharMingen (San Diego, Calif.) except anti-CD150-PE from Biolegend (San Diego, Calif.). For intracellular staining, cells were fixed and permeablized using Cytofix/Cytoperm solution (BD PharMingen), followed by P-Stat5 (pY694)-APC staining.

RNA Purification and Gene Expression Studies

RNA was isolated from thymus using the miRACLE™ total RNA isolation kit (Jinfiniti Biosciences) or RNeasy® kit (QIAGEN) and used for microarray and real-time RT-PCR analyses. The Illumina's MouseRef-8 v2.0 Expression BeadChip was used for transcriptional analysis. This BeadChip targets approximately 25,600 well-annotated RefSeq transcripts, over 19,100 unique genes, and enables the interrogation of eight samples in parallel. Probe preparation and hybridization were carried out according to Manufacture's recommendation. The microarray data are MIAME compliant and have been deposited in NCBI Gene Expression Omnibus and are accessible through GEO Series accession number GSE31526.

Differential expression analyses were conducted using the LIMMA (Linear Models for Microarray Analysis) package from the Bioconductor project (26). LIMMA uses an empirical Bayes approach that uses the variability in all genes for testing for significant differences, with this approach resulting in more stable inferences for a relatively small number of arrays (26, 27). The false discovery rate (FDR) adjustment was used for multiple testing (28) and a FDR cutoff of 1% is considered significant.

Real-time PCR was carried out in 96-well PCR plates using the ABI Prism 7900HT real-time PCR instrument (Applied Biosystems, Roche). The following primers, all from Applied Biosystems (Carlsbad, Calif.), were used: Stat5b, Ckmt2, Dgat2, Myl4, Csrp3, Nppa, Sln and Myh6. A final volume of 20 µl was used containing 2 µl of cDNA, 10 µl of TaqMan Master Mix (Roche, Minneapolis), 2 µl mix containing primers (200 nM of each primer, except for reference primers [20 nM]), 2 µl mix containing probes (100 nM of each probe), and water. The reaction was subjected to denaturation at 95° C. for 2 min, followed by 40 cycles of denaturation at 95° C. for 45 s and annealing/elongation at 60° C. for 1 min. Samples were tested in triplicate and negative and positive controls were included with each run. The fluorescent signal was measured at the end of the annealing/elongation step in each cycle.

Western Blotting

Whole cell extracts were prepared from thymus or spleens using RIPA lysis buffer (Santa Cruz) supplemented with protease inhibitors. Western blot analysis was carried out as reported (29) by probing the blots with rabbit anti-phospho-Stat5 (Tyr694), rabbit anti-Stat5 or mouse anti-β-actin (Santa Cruz biotechnology), washed, and incubated with a horseradish peroxidase-conjugated anti-rabbit or anti-mouse antibody (Santa Cruz biotechnology). Immunopositive bands were photographed (Versadoc; Bio-Rad) after blots were developed with an enhanced chemiluminescent substrate (Pierce Chemical Co).

Statistics

Pair-wise comparisons were made with Student t test. A probability (p) value was set at less than 0.05 for statistical significance.

Results

In order to examine the effect of Stat5b transgene and genetic background on lymphomagenesis, B6.Stat5b$^{Tg}$ mice were crossed with NOD mice and generated F1 Stat5b transgenic mice, designated as F1.Stat5b$^{Tg}$. Approximately 13% of these F1 mice developed lymphoma by 30 weeks of age (FIG. 1a), similar to the incidence reported for Stat5b transgenic mice in the B6 background (~12%) (7, 30). A NOD Stat5b transgenic line (NOD.Stat5b$^{Tg}$) was also generated through 21 generations of backcrossing with NOD mice. The NOD.Stat5b$^{Tg}$ mice spontaneously developed lymphoma. Lymphomas were observed as early as 10 weeks of age and reached an incidence of ~74% by 30 weeks of age (FIG. 1a). Mice with lymphomas have typically enlarged thymus, spleen, and lymph nodes, especially the cervical lymph node comparing to littermate controls (LMC) (FIG. 1b). Therefore, genes in the NOD genome can significantly increase the incidence of lymphoma and accelerate the disease when compared to the B6 or NOD/B6 F1 transgenic mice.

The lymphomas in NOD.Stat5b$^{Tg}$ mice were composed of sheets of intermediate-sized, blastic lymphoid cells that effaced the normal architecture of lymph nodes, spleen, and the thymus. The cellular morphology and the pattern of involvement of lymphoid organs mimic the features of lymphoblastic lymphoma in humans (FIG. 1c).

Figures 2A, 2B, 2C:
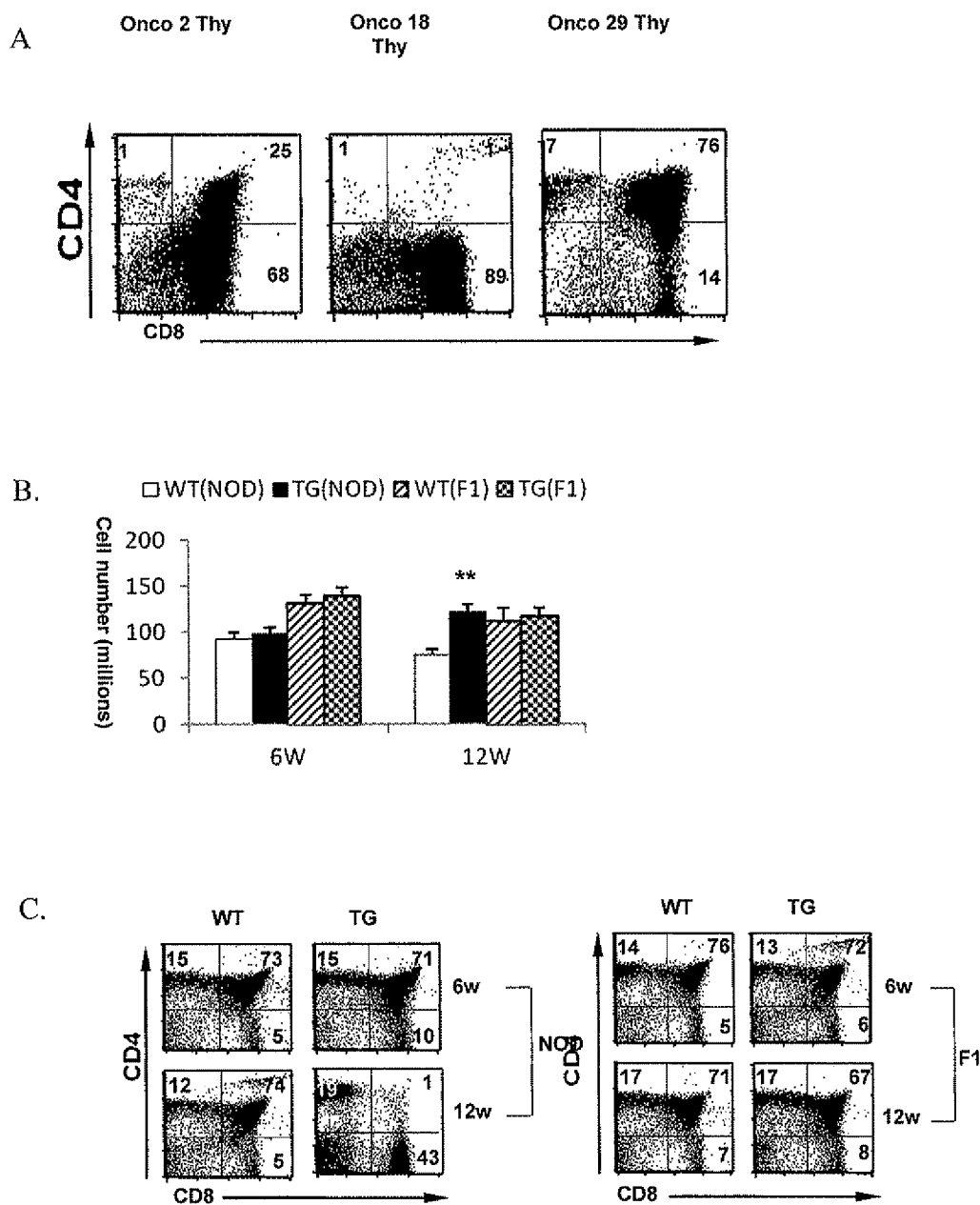
FIGS. 2a-c show phenotypes of CD8$^+$ lymphomas and T cell and B cell development in NOD.Stat5b$^{Tg}$ mice.

Of the 60 mice with lymphomas analyzed by flow cytometry, 57 mice had both CD4$^+$CD8$^+$ double positive and CDC single positive T cells, while two mice with lymphomas had predominantly CD8$^+$ cells and one mouse had predominantly CD4$^+$CD8$^+$ double positive cells in the thymus, spleen, and lymph nodes (FIG. 2a). Subcutaneous injection of malignant cells into regular NOD recipient mice resulted in tumor formation at the site of injection and migration to other lymphoid organs. Cells from these tumor masses and metastatic tumors had CD4/CD8 flow cytometric profiles indistinguishable from the original transplanted donor cells.

Example 2

STAT5B Promotes CD8$^+$ Thymocyte Expansion in NOD.Stat5b$^{Tg}$ Mice

Given that T cell lymphoma is of thymus origin, the cellular phenotypes in thymus of F1.Stat5b$^{Tg}$ mice were examined. Interestingly, the numbers and percentages of CD4$^+$ and CD8$^+$ thymocytes were similar in F1.Stat5b$^{Tg}$ mice and LMC (FIG. 2b) over time. These observations in the F1 mice are similar to the data reported for the Stat5b transgenic mice in the B6 background. The total numbers of thymocytes are also not significantly different at 6 weeks of age between NOD.Stat5b$^{Tg}$ mice and LMC. Surprisingly, by 12 weeks of age, the number and ratio of CD8$^+$ thymocytes dramatically increased in transgenic mice. In contrast, DP thymocytes in transgenic mice dramatically decreased by 12 weeks of age (FIGS. 2b & 2c).

Taken together, the impact of Stat5b transgene on CD8$^+$ thymocytes is only observed in the NOD background, but not in the B6 or NOD/B6 F1 background, suggesting that the NOD genome can synergize with Stat5b to promote CD8$^+$ thymocyte expansion.

Example 3

STAT5b is Increasingly Phosphorylated over Time in NOD.Stat5b$^{Tg}$ Mice

Why NOD.Stat5b$^{Tg}$ mice developed T cell lymphoma in much higher incidence and at earlier ages compared to both B6 and NOD/B6 F1 mice even though the same Stat5b transgene is present in these three different transgenic strains was investigated. Differences in STAT5 phosphorylation may account for the observed differences in lymphoma incidences in these strains. STAT5 phosphorylation (p-STAT5) was monitored using both FACS and Western blotting analysis. Similar to the observation in B6.Stat5b$^{Tg}$ mice (7), STAT5 phosphorylation was not detected in F1.Stat5b$^{Tg}$ mice without lymphoma (FIG. 3a) or with lymphoma (FIG. 3b), consistent with the observations of the low incidences of lymphoma observed in these strains. In contrast, Western blot and FACS analysis detected phosphorylated STAT5 protein at 6 weeks of age and increasing phosphorylation of STAT5 over time in the thymocytes of NOD.Stat5b$^{Tg}$ mice (FIGS. 3a & 3d). STAT5 phosphorylation was also detected in lymphoma cells from NOD.Stat5b$^{Tg}$ mice (FIG. 3b).

In order to differentiate the cell types in which STAT5 is phosphorylated, FACS was used to analyze phosphorylated STAT5 in different cell types in the spleens and thymus of NOD.Stat5b$^{Tg}$ mice. As shown in FIG. 3c, almost all CD8$^+$CD4$^-$ thymocytes stained positive for p-STAT5 and approximately one quarter of the CD8$^+$CD4$^+$ thymocytes also expressed, although at weaker levels, p-STAT5. However, CD4$^+$CD8$^-$ T cells and B cells had no detectable p-STAT5 (FIG. 3c). FACS analysis also confirmed that STAT5 phosphorylation in NOD.Stat5b$^{Tg}$ mice gradually increased over time and was detectable at early ages, at least around six weeks of age. These results, together, suggest that STAT5 is selectively activated in CD8$^+$ T cells in the NOD.Stat5b$^{Tg}$ mice.

Example 4

Screen of Candidate Genes and Proteins for STAT5b Induced Lymphomagenesis

To further dissect the molecular mechanisms underlying STAT5b-mediated lymphomagenesis, a global gene expression analysis was conducted using the Illumina gene chips with thymus tissues from four groups of mice at 4 weeks of age: 1) NOD.Stat5b$^{Tg}$, 2) non-transgenic littermates of NOD.Stat5b$^{Tg}$, 3) F1.Stat5b$^{Tg}$, and 4) non-transgenic littermates of the F1 transgenic mice. None of the mice had detectable tumor as evaluated by physical examination or FACS analysis. The microarray data have been deposited in NCBI Gene Expression Omnibus and are accessible through GEO Series accession number GSE31526.

Figure 4:
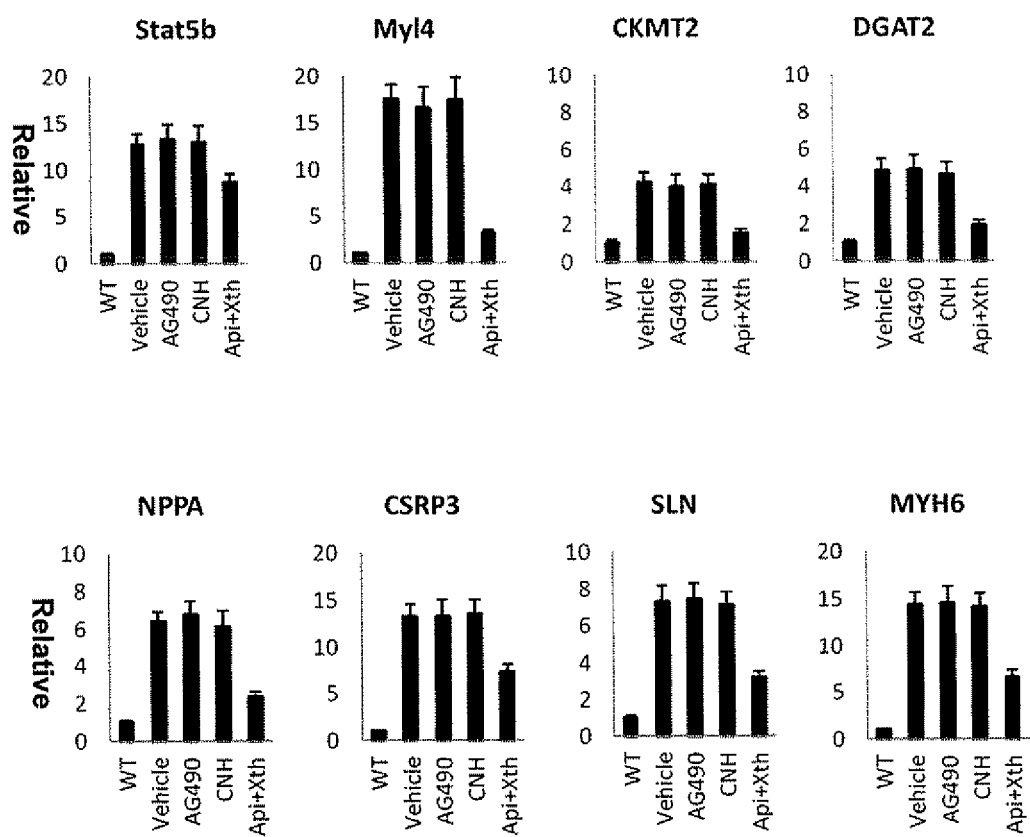
FIG. 4 is a panel of bar graphs showing the expression analysis of candidate genes in NOD.Stat5b$^{Tg}$ mice. Real-time RT-PCR was used to analyze RNA from thymus of vehicle NOD.Stat5b$^{Tg}$ mice (Vehicle) mice, and their littermate controls (WT) and NOD.Stat5b$^{Tg}$ mice after treatment with AG490, CNH and Apigenin plus Xanthohumol (Api+XN). RNA concentration was normalized with GAPDH. Data for WT were arbitrarily set to "1" for easier comparison. *P<0.05 and **P<0.01 for comparison between vehicle-treated NOD.Stat5b$^{Tg}$ mice and treatments.

Although STAT5 activation was not detectable in both F1 and NOD.Stat5b mice at 4 weeks of age, the global gene analysis revealed significant differences in the whole-genome expression profiles. The expression was increased by more than 2 folds for 56 genes in NOD.Stat5b$^{Tg}$ mice and 11 genes in F1.Stat5b$^{Tg}$ mice compared to their respective non-transgenic control mice, Some genes up-regulated in the NOD.Stat5b$^{Tg}$ mice were also highly expressed in the F1.Stat5b mice; however, it was that found 38 genes were up-regulated only in NOD.Stat5b$^{Tg}$ mice but not in F1.Stat5b$^{Tg}$ mice. The altered expression of 8 genes (Ckmt2, Dgat2, Myl4, Csrp3, Nppa, Sln and Myh6) in NOD.Stat5b$^{Tg}$ mice was confirmed using real-time RT-PCR analysis (FIG. 4). The up-regulation of these genes in the Stat5b transgenic mice is associated with both the transgene and the NOD genetic background. The data shows that the Stat5b transgene induces more gene expression changes in the NOD genetic background. These differentially expressed genes are implicated in cell proliferation, migration, energy production and many of these genes are also altered in various cancer patients.

An extensive screen for differences in cell surface markers on CD8$^+$ thymocytes was also carried out using the same four groups of mice. This FACS screen included more than 90 cell surface markers. Stat5b transgenic mice and their littermates at 4 weeks of age did not show significant differences for these proteins. However, CD150 was significantly up-regulated in NOD.Stat5b$^{Tg}$ but not in F1.Stat5b$^{Tg}$ mice starting at 6 weeks of age (FIG. 5a). These results show that the up-regulation of CD150 correlates with STAT5b activation in terms of both timing and mouse strains.

Example 5

Inhibition of STAT5 Pathway Leads to Decreases of CD8$^+$ Thymocyte Proliferation and CD150 Expression Because high CD150 expression was only observed in CD8$^+$ thymocytes in NOD.Stat5b$^{Tg}$ mice with detectable p-STAT5, it was hypothesized that STAT5 activation regulates CD150 expression. AG490 is a specific inhibitor for JAK2-STAT5 pathway, AG490 was examined to determine whether it could inhibit STAT5 activation. NOD.Stat5$^{Tg}$ mice at 10 weeks of age were treated with JAK2 inhibitor AG490 or vehicle (DMSO) for 2 weeks. AG490 treatment inhibited CD150 expression on CD8$^+$ thymocytes (FIG. 5b). Treatment with AG490 resulted in a dramatic decrease of p-STAT5 expression in thymocytes of NOD.Stat5b$^{Tg}$ mice as evaluated by Western analysis (FIG. 6a) and FACS analysis (FIG. 5b). These results show that CD150 expression correlates with STAT5 activation. Furthermore, AG490 greatly decreased the number of CD8$^+$ thymocytes (FIG. 5c). Consistent with this observation, AG490 treatment resulted in significantly increased apoptosis of lymphomas cells from NOD.Stat5b$^{Tg}$ mice in hallow fiber assays (FIG. 5d).

A recently developed STAT5-specific inhibitor [chromone-based nicotinyl hydrazone (CNH)] was also used to further examine the potential involvement of STAT5 in CD150 expression. This compound was reported to specifically inhibit STAT5 binding ability (31). Treatment with CNH for 2 weeks also significantly decreased the expression of CD150 on CD8$^+$ thymocytes (FIG. 5b) and the number of CD8$^+$ thymocytes (FIG. 5c). Furthermore, CNH treatment also resulted in significantly increased apoptosis of lymphoma cells from NOD.Stat5b$^{Tg}$ g mice in hallow fiber assay (FIG. 5d). As expected, CNH treatment did not decrease p-STAT5 expression level (FIG. 6a).

CD150 expression is very low on CD8$^+$ thymocytes from F1.Stat5$^{Tg}$ mice with or without lymphoma (FIG. 5a). In these mice, p-STAT5 was not detectable. Moreover, treatment with either AG490 or CNH did not alter the survival of CD8$^+$ lymphoma cells derived from F1.Stat5b$^{Tg}$ mice using the hollow fiber assay (data not shown). These results further substantiate the observation that STAT5 activation plays a critical role in CD150 expression.

Example 6

STAT5 Inhibitor Delays Lymphomagenesis

Since AG490 and STAT5b inhibitor CNH can inhibit STAT5 function and CD150 expression, they could delay lymphomagenesis. Previous studies suggested that STAT5 was important for the pathogenesis of many tumors. STAT5 inhibitors are potentially very effective in treating cancers with fewer unpleasant side effects. To test this possibility, CNH (40 mg/kg/day) was used to treat 5 week-old NOD.Stat5$^{Tg}$ mice with three cycles of 3-week on and 3-week off. The treated mice were free of lymphomas before 27 weeks of age and a significantly lower percentage (17%) of the treated mice developed lymphoma by 30 weeks of age (FIG. 1a).

Example 7

P-STAT5 and CD150 are Useful Biomarkers for Lymphoma Progression

Since blocking STAT5 activation and CD150 expression can delay lymphoma onset, these molecules can serve as biomarkers to identify novel cancer chemopreventive agents for lymphomas using the NOD.Stat5b$^{Tg}$ mouse model. The expression pattern of CD150 and pSTAT5 was monitored in CD8$^+$ T cells in peripheral blood, and it was confirmed that both CD150 and pSTAT5 were highly expressed in peripheral CD8$^+$ T cells of NOD.Stat5b$^{Tg}$ mice (FIGS. 6b & 6c). Furthermore, STAT5 pathway inhibitors decreased the expression of CD150 and pSTAT5 in peripheral CD8$^+$ T cells (FIG. 6b).

Subsequently, p-STAT5 and CD150 expression were analyzed in the peripheral blood CD8$^+$ T cells of 10-week old NOD.Stat5b$^{Tg}$ mice that were treated for 2 weeks with different compounds including Apigenin and Xanthohumol. These small molecules are contained in plants and have been reported to possess chemopreventive properties through multiple pathway (34, 35). These compounds can significantly inhibit STAT5 activation and CD150 expression (FIG. 6c).

Their potential ability to prevent lymphoma in the NOD.Stat5b$^{Tg}$ mice was further tested with three cycles of 3-week on and 3-week off treatment. The treated mice were free of lymphomas by 30 weeks of age (FIG. 1). Furthermore, Apigenin and Xanthohumol treatment significantly inhibited STAT5 activation and CD150 expression in CD8$^+$ thymocytes (FIG. 6d). These results suggest that the NOD.Stat5b$^{Tg}$ mouse model, together with the easily accessible biomarkers, provides an excellent tool for the in vivo screening and testing of anti-lymphoma chemopreventive drugs.

Additional genes implicated in lymphomagenesis were investigated by examining the expression of genes up-regulated in the NOD.Stat5b$^{Tg}$ mice (Ckmt2, Dgat2, Myl4, Csrp3, Nppa, Sln and Myh6). Interestingly, these genes in thymocytes were significantly decreased by Apigenin and Xanthohumol although the expression was not completely normalized to the level observed in LMC (FIG. 4). In contrast, AG490 or CNH treatment did not significantly down-regulate the expression of these representative genes in NOD.Stat5b$^{Tg}$ mice (FIG. 4). Therefore, these genes may not be essential to lymphomagenesis in the NOD.Stat5b$^{Tg}$ mice.

Discussion

The Stat5b transgene profoundly promotes CD8$^+$ thymocyte proliferation only in the NOD.Stat5b$^{Tg}$ mice in which STAT5 is strongly phosphorylated. These results show that the progressively increasing phosphorylation of STAT5 observed in thymocytes of NOD.Stat5b$^{Tg}$ mice but not in F1 or B6.Stat5b$^{Tg}$ mice may account for the differences in lymphoma incidences observed in these models. The precise reasons why STAT5 is phosphorylated in the NOD genetic background but not in 136 genetic background are still unknown. Interestingly, significantly increased IL-2Rβ on CD8$^+$ T cells and serum IL-2 concentration were observed in NOD.Stat5b$^{Tg}$ mice (data not shown). IL-2Rβ is regulated by STAT5b and reciprocally IL-2/IL-2Rβ can induce STAT5 phosphorylation.

An important difference between the strains is the phosphorylation of STAT5 that occurs selectively in CD8$^+$ T cells in the NOD.Stat5b$^{Tg}$ mouse model. These results suggest that STAT5 phosphorylation is very important to lymphomagenesis. A second difference between the strains is the rapid proliferation of CD8$^+$ thymocytes in the NOD but not in the B6 or F1 background, suggesting that other genes in the NOD genome synergize with the transgenic STAT5b to induce CD8$^+$ thymocytes proliferation. These results are consistent with the hypothesis on the thymus origin of T cell lymphoma (17, 18).

Unphosphorylated STATs may be partially functional in lymphomagenesis. Several researchers have already demonstrated unphosphorylated STATs drive gene expression by mechanisms distinct from those used by phosphorylated STAT dimers (41). Indeed, the global gene expression analysis also showed some differences between Stat5b transgenic mice and their littermate controls without detectable p-STAT5 in the F1 and NOD genetic backgrounds. However, STAT5 phosphorylation resulted in exacerbated T cell lymphomas.

The most likely mechanisms through which STAT5b could exert effects on expansion of T-lineage cells is through cooperation with pre-TCR (42-44), TCR (45, 46) and costimulatory signals or through its actions in transmitting signals from cytokines (47). Significantly higher expression of costimulatory molecules CD150 were observed over time in thymocytes and peripheral CD8$^+$ T cells of NOD.Stat5b$^{Tg}$ mice but not in B6 or F1.Stat5b$^{Tg}$ mice. CD150, also known as SLAM (Signaling Lymphocytic Activation Molecule), is a glycoprotein widely expressed at the transcriptional level in T, B, and myeloid cells and is rapidly up-regulated to the plasma membrane on activation of T cells and macrophages (48).

CD150 expression and p-STAT5 were reported in different types of lymphoma cell lines and patients(49). STAT5 activation was found to up-regulate CD150 expression and promote CD8$^+$ thymocytes proliferation. The data showed that CD150 and p-STAT5 could serve as biomarkers for lymphomagenesis and also for monitoring therapeutic outcomes of lymphoma therapy. These conclusions are substantiated by the observations that treatment with either STAT5 pathway specific inhibitor or cancer chemopreventive agents (API and XN) resulted in a decrease of CD150 expression, STAT5 phosphorylation and a nearly complete prevention of lymphoma.

Overexpression of the Stat5b gene could induce T cell lymphomas with different incidences, age of onset and phenotypes in different genetic backgrounds. In the NOD genetic background, STAT5b is selectively and progressively phosphorylated in CD8$^+$ thymocytes, resulting in CD8$^+$ thymocytes proliferation and high incidence of T cell lymphoma. Furthermore, CD150 expression on CD8$^+$ T cells correlates with STAT5b activation and may be an essential molecule implicated in CD8$^+$ T cell proliferation and lymphomagenesis. Monitoring of p-STAT5 and CD150 in the peripheral blood CD8$^+$ T cells was an efficient strategy to screen chemopreventive agents for T cell lymphomas. Since p-STAT5 and CD150 are highly expressed in many human lymphoma cell lines and patients, the data suggest that p-STAT5 and CD150 are also excellent biomarkers for lymphomagenesis and therapeutic outcomes for certain lymphomas in human.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1. Yang J, Stark G R. Roles of unphosphorylated STATs in signaling. Cell research. 2008 April; 18(4):443-451.
2. Ihle J N, Kerr I M. Jaks and Stats in signaling by the cytokine receptor superfamily. Trends Genet. 1995 February; 11(2):69-74.
3. Shuai K, Horvath C M, Huang L H, Qureshi S A, Cowburn D, Darnell J E, Jr. Interferon activation of the transcription factor Stat91 involves dimerization through SH2-phosphotyrosyl peptide interactions. Cell. 1994 Mar. 11; 76(5): 821-828.
4. Kabbarah O, Chin L. Revealing the genomic heterogeneity of melanoma. Cancer cell. 2005 December; 8(6):439-441.
5. Pecquet C, Staerk J, Chaligne R, Goss V, Lee K A, Zhang X, Rush J, Van Hees J, Poirel H A, Scheiff J M, Vainchenker W, Giraudier S, Polakiewicz R D, Constantinescu S N. Induction of myeloproliferative disorder and myelofibrosis by thrombopoietin receptor W515 mutants is mediated by cytosolic tyrosine 112 of the receptor. Blood. February 4; 115(5):1037-1048.
6. Wang Y, Cai D, Brendel C, Barett C, Erben P, Manley P W, Hochhaus A, Neubauer A, Burchert A. Adaptive secretion of granulocyte-macrophage colony-stimulating factor (GM-CSF) mediates imatinib and nilotinib resistance in BCR/ABL+ progenitors via JAK-2/STAT-5 pathway activation. Blood. 2007 Mar. 1; 109(5):2147-2155.
7. Kelly J A, Spolski R, Kovanen P E, Suzuki T, Bollenbacher J, Pise-Masison C A, Radonovich M F, Lee S, Jenkins N A, Copeland N G, Morse H C, 3rd, Leonard W J. Stat5 synergizes with T cell receptor/antigen stimulation in the development of lymphoblastic lymphoma. The Journal of experimental medicine. 2003 Jul. 7; 198(1):79-89.
8. O'Shea J J. Jaks, STATs, cytokine signal transduction, and immunoregulation: are we there yet? Immunity. 1997 July; 7(1):1-11.
9. Moriggl R, Sexl V, Kenner L, Duntsch C, Stangl K, Gingras S, Hoffmeyer A, Bauer A, Piekorz R, Wang D, Bunting K D, Wagner E F, Sonneck K, Valent P, Ihle J N, Beug H. Stat5 tetramer formation is associated with leukemogenesis. Cancer cell. 2005 January; 7(1):87-99.
10. Nikitakis N G, Siavash H, Sauk J J. Targeting the STAT pathway in head and neck cancer: recent advances and future prospects. Current cancer drug targets. 2004 December; 4(8):637-651.
11. Rouet V, Bogorad R L, Kayser C, Kessal K, Genestie C, Bardier A, Grattan D R, Kelder B, Kopchick J J, Kelly P A, Goffin V. Local prolactin is a target to prevent expansion of basal/stem cells in prostate tumors. Proceedings of the National Academy of Sciences of the United States of America. August 24; 107(34):15199-15204.
12. Sordella R, Bell D W, Haber D A, Settleman J. Gefitinib-sensitizing EGFR mutations in lung cancer activate anti-apoptotic pathways. Science (New York, N.Y. 2004 Aug. 20; 305(5687):1163-1167.
13. Tang J Z, Zuo Z H, Kong X J, Steiner M, Yin Z, Perry J K, Zhu T, Liu D X, Lobie P E. Signal transducer and activator of transcription (STAT)-5A and STAT5B differentially regulate human mammary carcinoma cell behavior. Endocrinology. January; 151(1):43-55.
14. Fantin V R, Loboda A, Paweletz C P, Hendrickson R C, Pierce J W, Roth J A, Li L, Gooden F, Korenchuk S, Hou X S, Harrington E A, Randolph S, Reilly J F, Ware C M, Kadin M E, Frankel S R, Richon V M. Constitutive activation of signal transducers and activators of transcription predicts vorinostat resistance in cutaneous T-cell lymphoma. Cancer research. 2008 May 15; 68(10):3785-3794.
15. Peck A R, Witkiewicz A K, Liu C, Stringer G A, Klimowicz A C, Pequignot E, Freydin B, Tran T H, Yang N, Rosenberg A L, Hooke J A, Kovatich A J, Nevalainen M T, Shriver C D, Hyslop T, Sauter G, Rimm D L, Magliocco A M, Rui H. Loss of nuclear localized and tyrosine phosphorylated stat5 in breast cancer predicts poor clinical outcome and increased risk of antiestrogen therapy failure. J Clin Oncol. June 20; 29(18):2448-2458.
16. Tweardy D, Chang J C. Stat5: from breast development to cancer prognosis, prediction, and progression. J Clin Oncol. June 20; 29(18):2443-2444.
17. Aifantis I, Raetz E, Buonamici S. Molecular pathogenesis of T-cell leukaemia and lymphoma. Nature reviews. 2008 May; 8(5):380-390.
18. Serwold T, Hochedlinger K, Swindle J, Hedgpeth J, Jaenisch R, Weissman I L. T-cell receptor-driven lymphomagenesis in mice derived from a reprogrammed T cell. Proceedings of the National Academy of Sciences of the United States of America. November 2; 107(44):18939-18943.
19. Catovsky D, Greaves M F, Rose M, Galton D A, Goolden A W, McCluskey D R, White J M, Lampert I, Bourikas G, Ireland R, Brownell A I, Bridges J M, Blattner W A, Gallo R C. Adult T-cell lymphoma-leukaemia in Blacks from the West Indies. Lancet. 1982 Mar. 20; 1(8273):639-643.
20. Han X, Kilfoy B, Zheng T, Holford T R, Zhu C, Zhu Y, Zhang Y. Lymphoma survival patterns by WHO subtype in the United States, 1973-2003. Cancer Causes Control. 2008 October; 19(8):841-858.
21. Hinds G A, Heald P. Cutaneous T-cell lymphoma in skin of color. Journal of the American Academy of Dermatology. 2009 March; 60(3):359-375; quiz 376-358.
22. Weber-Nordt R M, Egen C, Wehinger J, Ludwig W, Gouilleux-Gruart V, Mertelsmann R, Finke J. Constitutive activation of STAT proteins in primary lymphoid and myeloid leukemia cells and in Epstein-Barr virus (EBV)-related lymphoma cell lines. Blood. 1996 Aug. 1; 88(3):809-816.
23. Davoodi-Semiromi A, McDuffie M, Litherland S, Clare-Salzler M. Truncated pStat5B is associated with the Idd4 locus in NOD mice. Biochemical and biophysical research communications. 2007 May 11; 356(3):655-661.
24. Litherland S A, Grebe K M, Belkin N S, Paek E, Elf J, Atkinson M, Morel L, Clare-Salzler M J, McDuffie M. Nonobese diabetic mouse congenic analysis reveals chromosome 11 locus contributing to diabetes susceptibility, macrophage STAT5 dysfunction, and granulocyte-macrophage colony-stimulating factor overproduction. J Immunol. 2005 Oct. 1; 175(7):4561-4565.
25. Kelly J, Spolski R, Imada K, Bollenbacher J, Lee S, Leonard W J. A role for Stat5 in CD8+ T cell homeostasis. J Immunol. 2003 Jan. 1; 170(1):210-217.
26. Smyth G K. Linear models and empirical bayes methods for assessing differential expression in microarray experiments. Statistical applications in genetics and molecular biology. 2004; 3: Article3.
27. Kerr K F. Comments on the analysis of unbalanced microarray data. Bioinformatics (Oxford, England). 2009 Aug. 15; 25(16):2035-2041.
28. Zawistowski M, Gopalakrishnan S, Ding J, Li Y, Grimm S, Zollner S. Extending rare-variant testing strategies: analysis of noncoding sequence and imputed genotypes. American journal of human genetics. November 12; 87(5): 604-617.
29. Lebigot I, Gardellin P, Lefebvre L, Beug H, Ghysdael J, Quang C T. Up-regulation of SLAP in FLI-1-transformed erythroblasts interferes with EpoR signaling. Blood. 2003 Dec. 15; 102(13):4555-4562.
30. Bessette K, Lang M L, Fava R A, Grundy M, Heinen J, Horne L, Spolski R, Al-Shami A, Morse H C, 3rd, Leonard W J, Kelly J A. A Stat5b transgene is capable of inducing CD8+ lymphoblastic lymphoma in the absence of normal TCR/MHC signaling. Blood. 2008 Jan. 1; 111(1):344-350.
31. Muller J, Sperl B, Reindl W, Kiessling A, Berg T. Discovery of chromone-based inhibitors of the transcription factor STAT5. Chembiochem. 2008 Mar. 25; 9(5):723-727.
32. Cui Y, Riedlinger G, Miyoshi K, Tang W, Li C, Deng C X, Robinson G W, Hennighausen L. Inactivation of Stat5 in mouse mammary epithelium during pregnancy reveals distinct functions in cell proliferation, survival, and differentiation. Molecular and cellular biology. 2004 September; 24(18):8037-8047.
33. Wang Z, Li G, Tse W, Bunting K D. Conditional deletion of STAT5 in adult mouse hematopoietic stem cells causes loss of quiescence and permits efficient nonablative stem cell replacement. Blood. 2009 May 14; 113(20):4856-4865.
34. Gerhauser C, Alt A, Heiss E, Gamal-Eldeen A, Klimo K, Knauft J, Neumann I, Scherf H R, Frank N, Bartsch H, Becker H. Cancer chemopreventive activity of Xanthohumol, a natural product derived from hop. Molecular cancer therapeutics. 2002 September; 1(11):959-969.
35. Shukla S, Gupta S. Apigenin: a promising molecule for cancer prevention. Pharmaceutical research. June; 27(6): 962-978.
36. Bunting K D. STAT5 signaling in normal and pathologic hematopoiesis. Front Biosci. 2007; 12:2807-2820.
37. Burchill M A, Goetz C A, Prlic M, O'Neil J J, Harmon I R, Bensinger S J, Turka L A, Brennan P, Jameson S C, Farrar M A. Distinct effects of STAT5 activation on CD4+ and CD8+ T cell homeostasis: development of CD4+CD25+ regulatory T cells versus CD8+ memory T cells. J Immunol. 2003 Dec. 1; 171(11):5853-5864.
38. Joliot V, Cormier F, Medyouf H, Alcalde H, Ghysdael J. Constitutive STAT5 activation specifically cooperates with the loss of p53 function in B-cell lymphomagenesis. Oncogene. 2006 Aug. 3; 25(33):4573-4584.
39. Davoodi-Semiromi A, Laloraya M, Kumar G P, Purohit S, Jha R K, She J X. A mutant Stat5b with weaker DNA binding affinity defines a key defective pathway in non-obese diabetic mice. The Journal of biological chemistry. 2004 Mar. 19; 279(12):11553-11561.
40. Laloraya M, Davoodi-Semiromi A, Kumar G P, McDuffie M, She J X. Impaired Crk1 expression contributes to the defective DNA binding of Stat5b in nonobese diabetic mice. Diabetes. 2006 March; 55(3):734-741.
41. Cheon H, Stark G R. Unphosphorylated STAT1 prolongs the expression of interferon-induced immune regulatory genes. Proceedings of the National Academy of Sciences of the United States of America. 2009 Jun. 9; 106(23): 9373-9378.
42. Canon C, Cormier F, Janin A, Lacronique V, Giovannini M, Daniel M T, Bernard O, Ghysdael J. TEL-JAK2 transgenic mice develop T-cell leukemia. Blood. 2000 Jun. 15; 95(12):3891-3899.
43. dos Santos N R, Rickman D S, de Reynies A, Cormier F, Williame M, Blanchard C, Stern M H, Ghysdael J. Pre-TCR expression cooperates with TEL-JAK2 to transform immature thymocytes and induce T-cell leukemia. Blood. 2007 May 1; 109(9):3972-3981.
44. Schwaller J, Parganas E, Wang D, Cain D, Aster J C, Williams I R, Lee C K, Gerthner R, Kitamura T, Frantsve J, Anastasiadou E, Loh M L, Levy D E, Ihie, J N, Gilliland D G. Stat5 is essential for the myelo- and lymphoproliferative disease induced by TEL/JAK2. Molecular cell. 2000 September; 6(3):693-704.
45. Klinger M B, Guilbault B, Goulding R E, Kay R J. Deregulated expression of RasGRP1 initiates thymic lymphomagenesis independently of T-cell receptors. Oncogene. 2005 Apr. 14; 24(16):2695-2704.
46. Yu C L, Jove R, Burakoff S J. Constitutive activation of the Janus kinase-STAT pathway in T lymphoma overexpressing the Lck protein tyrosine kinase. J Immunol. 1997 Dec. 1; 159(11):5206-5210.
47. Yao Z, Cui Y, Watford W T, Bream J H, Yamaoka K, Hissong B D, Li D, Durum S K, Jiang Q, Bhandoola A, Hennighausen L, O'Shea J J. Stat5a/b are essential for normal lymphoid development and differentiation. Proceedings of the National Academy of Sciences of the United States of America. 2006 Jan. 24; 103(4):1000-1005.
48. Wang N, Campo M, Ting L, Fleming C, Terhorst C, Finn P W. The costimulatory molecule SLAM is critical for pulmonary allergic responses. American journal of respiratory cell and molecular biology. 2006 August; 35(2):206-210.
49. Heinzerling L, Kunzi V, Oberholzer P A, Kundig T, Naim H, Dummer R. Oncolytic measles virus in cutaneous T-cell lymphomas mounts antitumor immune responses in vivo and targets interferon-resistant tumor cells. Blood. 2005 Oct. 1; 106(7):2287-2294.

We claim:

1. A transgenic non-obese diabetic (NOD) mouse whose genome comprises a constitutively active form of the STAT5b transgene, wherein overexpression of the STAT5b transgene promotes CD8 (+) thymocyte expansion.

2. A method for identifying therapeutic agents for the treatment of hematological malignancies comprising: administering a test compound to transgenic non-obese diabetic (NOD) mouse whose genome comprises a constitutively active form of the STAT5b transgene, wherein overexpression of the STAT5b transgene promotes CD8(+) thymocyte expansion; determining the presence or absence of hematological malignancies or symptoms thereof in the NOD mouse after administration of the test compound, wherein a reduced amount of hematological malignancies, symptoms, or biomarkers thereof in the NOD mouse after treatment with the test compound is indicative that the test compound is a therapeutic agent for the treatment of the hematological malignancies.

3. The method of claim 2, wherein the biomarker is CD 150.

* * * * *